United States Patent
Mathieu et al.

(10) Patent No.: US 9,770,505 B2
(45) Date of Patent: Sep. 26, 2017

(54) VACCINE COMPOSITION WITH ALUMINIUM HYDROXIDE NANOPARTICLES

(75) Inventors: Yannick Mathieu, Colmar (FR); Benedicte Lebeau, Wattwiller (FR); Valentin Valtchev, Basly (FR); Joel Patarin, Flaxlanden (FR); Marie Garinot, Lyons (FR); Jean Haensler, Grezieu la Varenne (FR); Elisabeth Sauzeat, Lentilly (FR)

(73) Assignee: SANOFI PASTEUR, Lyons (FR)

( * ) Notice: Subject to any disclaimer, the term of this patent is extended or adjusted under 35 U.S.C. 154(b) by 333 days.

(21) Appl. No.: 14/131,616

(22) PCT Filed: Jul. 12, 2012

(86) PCT No.: PCT/FR2012/051648
§ 371 (c)(1),
(2), (4) Date: Apr. 30, 2014

(87) PCT Pub. No.: WO2013/007956
PCT Pub. Date: Jan. 17, 2013

(65) Prior Publication Data
US 2014/0234422 A1 Aug. 21, 2014

(30) Foreign Application Priority Data
Jul. 13, 2011 (FR) ..................................... 11 56398

(51) Int. Cl.
*A61K 39/39* (2006.01)
*A61K 9/51* (2006.01)
*A61K 39/145* (2006.01)
*A61K 39/08* (2006.01)
*A61K 39/12* (2006.01)
*A61K 39/00* (2006.01)

(52) U.S. Cl.
CPC ............ *A61K 39/39* (2013.01); *A61K 9/5115* (2013.01); *A61K 39/08* (2013.01); *A61K 39/12* (2013.01); *A61K 39/145* (2013.01); *A61K 2039/55505* (2013.01); *A61K 2039/55511* (2013.01); *A61K 2039/55555* (2013.01); *A61K 2039/57* (2013.01); *A61K 2039/64* (2013.01); *A61K 2039/70* (2013.01); *C12N 2760/16134* (2013.01); *C12N 2760/16234* (2013.01)

(58) Field of Classification Search
None
See application file for complete search history.

(56) References Cited

U.S. PATENT DOCUMENTS

| 4,269,821 A | 5/1981 | Kreuter et al. |
| 4,836,948 A * | 6/1989 | Corring ................. A61K 8/042 510/223 |
| 2005/0158334 A1 | 7/2005 | Contorni et al. |

FOREIGN PATENT DOCUMENTS

| EP | 1 126 876 | 8/2001 | |
| WO | 94/15636 | 7/1994 | |
| WO | 2007/052058 | 5/2007 | |
| WO | WO2007/052058 | * 5/2007 | ........... A61K 39/145 |
| WO | 2008/109852 | 9/2008 | |
| WO | 2009/012601 A1 | 1/2009 | |
| WO | 2010/119343 A2 | 10/2010 | |

OTHER PUBLICATIONS

Mathieu et al. (J. Phys. Chem. 2008, vol. 112, p. 18384-18392).*
Yau et al. (Journal of Pharmaceutical Sciences, 2006, vol. 95, p. 1822-1833).*
Stieneker et al., "Comparison of 24 different adjuvants for inactivated HIV-2 split whole virus as antigen in mice. Induction of titres of binding antibodies and toxicity of the formulations," Vaccine, Elsevier Ltd, GB, vol. 13, No. 1, Jan. 1, 1995, pp. 45-53.
Mathieu et al., "Control of the Morphology and Particle Size of Boehmite Nanoparticles synthesied under Hydrothermal Conditions," Langmuir, vol. 23, No. 18, Aug. 1, 2007, pp. 9435-9442.
Kwok Pan Yau et al., "Aluminum hydroxide adjuvant produced under constant reactant concentration," Journal of Pharmaceutical Sciences, vol. 95, No. 8, Aug. 1, 2006, pp. 1822-1833.
Coiai et al., "Organophilic Boehmite nanoparticles by ATRP methacrylates polymerization: synthesis, characterization and dispersion in polypropylene," Journal of Nanoscience and Nanotechnology, American Scientific Publishers, US, vol. 8, No. 4, Apr. 1, 2008, pp. 1803-1811.
Alphonse et al., "Surface and porosity of nanocrystalline boehmite xerogels," Journal of Colloid and Interface Science, Academic Press, NY, NY, US, vol. 290, No. 1, Oct. 1, 2005, pp. 208-219.

* cited by examiner

*Primary Examiner* — Agnieszka Boesen
(74) *Attorney, Agent, or Firm* — McDonnell Boehnen Hulbert & Berghoff LLP

(57) ABSTRACT

A vaccine composition comprising at least one antigen and one adjuvant, characterized in that the adjuvant comprises sterile-filterable nanoparticles comprising pseudo-boehmite and polyacrylate.

18 Claims, No Drawings

VACCINE COMPOSITION WITH ALUMINIUM HYDROXIDE NANOPARTICLES

This application is a US national phase of International Application No. PCT/FR2012/051648 filed on Jul. 12, 2012, which claims the benefit of French application No. 1156398 filed Jul. 13, 2011.

The present invention relates to the field of vaccines and more particularly to vaccine compositions comprising at least one adjuvant. In particular, the invention relates to a vaccine composition comprising nanoparticles which can be sterile filtered, comprising pseudo-boehmite and polyacrylate (PAA).

It has been known for a very long time in the prior art that aluminum is advantageous for adjuvating vaccines. Many commercial vaccines contain the same, either in hydroxide form or in the form of phosphates; these names, moreover, not exactly reflecting the chemical composition of the corresponding products: the aluminum hydroxides are rather oxyhydroxides, and the aluminum phosphates are rarely pure phosphates, but very often contain other ions, especially sulfates, and also hydroxides. Although these aluminum-based adjuvants, also known as aluminum gels, have shown their entire advantage for increasing the immune response induced by an antigen, they do, however, have certain drawbacks. From an industrial viewpoint, conventional suspensions of aluminum hydroxide or phosphate do not, on account of the excessively large particle size, make it possible to perform at the end of production sterilization by filtration, and thus demand recourse to a production process proceeding under aseptic conditions. Moreover, in the case of certain modes of administration, especially intradermally, aluminum has been reproached for leading to a tattoo effect at the site of administration. It is thus desirable to have available vaccine compositions comprising aluminum in order to benefit from its adjuvant powers, while at the same time avoiding its drawbacks. To this end, the present invention proposes a vaccine composition comprising at least one antigen and an adjuvant, characterized in that the adjuvant comprises nanoparticles which can be sterile filtered, comprising pseudo-boehmite and polyacrylate.

A subject of the present invention is also the use of nanoparticles which can be sterile filtered, comprising pseudo-boehmite and polyacrylate, for the preparation of a vaccine composition comprising at least one antigen.

In particular, the invention has for the use of such nanoparticles which make it possible to increase the immune response induced during the administration of said vaccine composition.

A subject of the present invention is also a process for preparing a vaccine composition comprising at least one antigen and an adjuvant, according to which:
  nanoparticles which can be sterile filtered, comprising pseudo-boehmite and polyacrylate, are prepared,
  said nanoparticles are filtered by means of a sterilizing filter,
  at least one vaccine antigen is added to said nanoparticles,
  and, optionally, an additional filtration is performed, if necessary.

By means of the subject of the invention, it is possible to have a vaccine adjuvant which induces less of a reactogenicity reaction than the aluminum suspensions conventionally used, especially after intradermal (ID) administration, and which makes it possible at the end of the manufacturing process to perform sterilization via filtration.

Other advantages of the invention will emerge in the course of the description that follows.

Within the terms of the present invention, nanoparticles are particles whose size allows them to pass through a sterilizing filter, the pores of which have a diameter of 220 nm. The particles thus have a size of less than 300 nm, since such particles can pass through pores of smaller size by deformation. However, preferably, the particles have a size of less than 220 nm, and, even, less than 200 nm. Such particles form colloidal suspensions that are transparent. Advantageously, suspensions are used in which the majority of the particles are between 30 and 200 nm in diameter, which allows them to be filtered without excessive loss of material, with a sterilizing filter whose cut-off threshold is 220 nm. The diameter of the particles is a hydrodynamic diameter, which may be measured via various techniques: for example, quasi-elastic light scattering may be used. This technique makes it possible to measure the size of the particles in a colloidal suspension for radii ranging from 1 nanometer to several micrometers. Particles in suspension in a liquid are subject to Brownian motion (thermal agitation and impacts between molecules of the liquid and solid particles). The principle of a light scattering measurement consists in bombarding the particles in the colloidal suspension with coherent and monochromatic radiation of laser type and then in recording the fluctuations in light intensity scattered by these particles by means of an avalanche photodiode (device for counting the number of photons).

These experiments usually take place in very dilute media that are transparent to the eye. In the case of the present invention, the diameter of the nanoparticles was determined after dilution (generally 1/10) in demineralized water. The model of machine used was a Malvern ZetaSizer Nano ZS.

According to the invention, the nanoparticles are particles consisting essentially of pseudo-boehmite with polyacrylate at their surface to prevent aggregation of the nanoparticles after washing of the nanoparticles by dialysis. According to a particular mode of the invention, the polyacrylate is bonded to the pseudo-boehmite via interactions of electrostatic type. According to one mode of the invention, the amount of polyacrylate represents a mass of less than 10% of the mass of the nanoparticles, more particularly a mass of less than 9%, 8%, 7%, 6%, 5%, 4%, 3%, 2%, 1%. According to one mode of the invention, the amount of polyacrylate represents a mass at least equal to 1% of the mass of the nanoparticles, more particularly a mass of greater than 2%, 3%, 4%, 5%, 6%, 7%, 8%, 9%.

In the qualification of the essential constituent of the nanoparticles of the invention as pseudo-boehmite may be performed by X-ray diffraction analysis, which gives an X-ray diffractogram characteristic of pseudo-boehmite with the main lines (020), (021), (130), (150), (151) and (132) observed at 14, 28.1, 32.4, 49.3, 55.5 and 65° 2θ (λ=0.15406 nm).

Polyacrylate is used since the polymers used must be biocompatible, i.e. they must show no toxicity toward the organism to which they are administered. In addition, the polymer used must be stable at the temperatures used during the synthesis of the nanoparticles. The polyacrylate used may be of various molecular weights; it may especially be sodium polyacrylate or a polyacrylate of any other salt that is suitable for pharmaceutical use. Good results were obtained with the sodium polyacrylate PAA 2100 supplied by the company Fluka, and also with PAA-60 000 from Polysciences.

The particles are prepared according to a method inspired by the method described by S. Musić et al. in *Materials*

Chemistry and Physics, 1999, 59, 12-19 entitled *Chemical and microstructural properties of Al-oxide phases obtained from AlCl₃ solutions in alkaline medium*. According to S. Musić et al., the pH of an aqueous solution of aluminum salt is increased by adding a base (NaOH) up to a value slightly above 11 over a period of 5 minutes (controlled using a pH-meter). Next, the mixture is stirred vigorously for 10 minutes and then transferred into an autoclave and heated at 160° C. for 24 hours. The product (homogeneous whitish solution) is recovered by Büchner filtration, washed and then dried overnight in an oven at 65° C. In the case of the syntheses according to the present invention, and as was described by Y. Mathieu et al. in *Control of the morphology and particle size of boehmite nanoparticles synthesized under hydrothermal conditions* in Langmuir 2007, 23, 9435-9442, the synthesis is performed in the presence of sodium polyacrylate, which is added at the start to the aqueous solution of aluminum salts. The presence of polymer prevents the agglomeration of the particles formed. The relative amounts of polyacrylate and of aluminum salt are selected so as to be able to dissolve the polyacrylate in the aluminum salt solution and to obtain filterable nanoparticles suitable for use as vaccine adjuvant. It was thus noted that with PAA 2100, it was advantageous to adhere to a mole ratio of sodium polyacrylate to aluminum of between 0.43 and 0.57.

Before adding the base, the mixture of sodium polyacrylate and aluminum salt is subjected to a maturation phase during which it is stirred. This maturation phase is advantageously performed at room temperature for about 24 hours. From an industrial viewpoint, it is very advantageous to be able to work at room temperature, over a short period, which may be prolonged if necessary, for example over weekends.

The aluminum salts for producing nanoparticles may be of diverse nature; they may especially be aluminum chloride $AlCl_3$, aluminum nitrate $Al(NO_3)_3$ or aluminum sulfate $Al_2(SO_4)_3$; aluminum chloride $AlCl_3$ is preferably chosen.

The bases that may be used for increasing the pH of the mixture are diverse and may be chosen especially from NaOH, KOH and $NH_4OH$. Advantageously, the synthesis of the nanoparticles is performed using sodium hydroxide NaOH.

According to the invention, sodium hydroxide is used to increase the pH up to a value of about 10-11 during an operation lasting between 5 and 10 minutes. During this pH increase phase, the various aluminum species present undergo changes, such as dissociations and rearrangements to result in the formation of a more or less crystalline phase.

According to the invention, the mixture is then subjected to a hydrothermal treatment for a period that may range from 1 to 17 hours; advantageously, with regard to the size of the particles obtained and to their filterability, a duration of 3 hours is chosen. This treatment is performed either in static mode, or with stirring at a temperature of between 90° C. and 200° C., more particularly at 160° C.

According to the invention, the nanoparticles obtained can be sterile filtered, which means that they have a size which enables them to pass through a sterilizing filter whose pore size is 220 nm; the losses observed during such a filtration are compatible with industrial constraints. Specifically, tests performed on 0.22 μm PTFE (polytetrafluoroethylene) filters showed that less than 5% loss of polymer and of aluminum occurred, this value of 5% possibly corresponding to the margin of error of the assay technique.

According to the invention, the nanoparticles may be in suspension in a saline solution or a biological buffer. Tests were especially performed in PBS (phosphate-buffered saline) buffer, in TRIS (tris(hydroxymethyl)aminomethane) buffer or in a saline solution comprising 90 g/l of NaCl, 0.12 g/l of $Na_2HPO_4$ and 0.6 g/l of $KH_2PO_4$.

According to a particular characteristic of the invention, the suspension comprising the nanoparticles of pseudo-boehmite and of polyacrylate also comprises a surfactant, especially a neutral surfactant such as Brij™ 58, Pluronic™ 123 or Tween™ 60, or an anionic surfactant such as SDS (sodium dodecyl sulfate), or alternatively a polymer such as PEG (polyethylene glycol). Thus, the stabilization of the nanoparticles formed may be increased via a steric effect or via electrostatic repulsion.

According to the invention, the vaccine composition comprises at least one antigen. For the purposes of developing the present invention, a purified tetanus protein was used as model antigen. Tests were then performed with other antigens, especially influenza antigens, the malaria antigen LSA3, or alternatively ETEC (Enterotoxigenic *Escherichia coli*) recombinant antigens. However, the vaccine composition according to the invention may comprise any antigen that may be used in a vaccine, whether it is a whole microorganism, a subunit antigen, which is natural, recombinant, hybrid, etc., irrespective of its nature; the antigen may in fact be a peptide, a protein, a glycoprotein, a polysaccharide, a glycolipid, a lipopeptide, a VLP (virus-like particle), etc.

These antigens are antigens that are used or that may be used for treating or preventing various diseases liable to affect the animal kingdom and in particular human beings, especially: diphtheria, tetanus, polio, rabies, whooping cough, hepatitis A, B or C, yellow fever, typhoid fever, chicken pox, measles, mumps, German measles, Japanese encephalitis, influenza, meningitis, cholera, infections mediated by: Rotavirus, Norovirus, Rhinovirus, Respiratory Syncytial Virus, Herpes Simplex Virus, Papilloma Virus, Cytomegalovirus, West Nile Virus, Dengue Virus, Chykungunya Virus, HIV (AIDS), bacterial complaints brought about by: streptococci, *Chlamydia trachomatis* and *pneumoniae*, *Neisseria gonorrheae* and *meningitidis*, *Moraxella catarrhalis*, *Staphylococcus aureus* or *Haemophilus influenza* type B, listeriosis, shigellosis, salmonellosis, tuberculosis, Lyme's disease, cancer, parasitic complaints such as malaria, leishmaniasis, etc.

The pharmaceutical composition according to the invention may be a composition for immunization against a single pathogen or cancer, i.e. it comprises one or more antigens of a single pathogen or cancer, or alternatively may be a composition for immunization against several pathogens or cancers (in which case it is referred to as a vaccine combination). The composition according to the invention may also comprise several antigens specific for a single disease, but belonging to different categories of the agent of this disease (several strains or serotypes, or clades, depending on the nature of the agent). It may also be a vaccine composition comprising allergens, intended especially for desensitization in the field of treating allergies.

The vaccine composition according to the invention may be administered via any route usually used for the administration of vaccines; however, the intradermal route is of particular interest. Specifically, although it seems very efficient for inducing good immune reactions, the intradermal route has the drawback of occasionally leading to local reactogenicity reactions, which may hinder its use. By virtue of the nanoparticles according to the invention, it was possible to perform intradermal immunizations having very little or no reactogenicity reaction, and especially no tattoo effect as might have been the case with the aluminum suspensions of the prior art.

According to the invention, the vaccine composition is prepared by simple mixing of a suspension comprising the nanoparticles of pseudo-boehmite and of polyacrylate and an antigen suspension. This operation may take place by adding antigens to a colloidal suspension comprising the nanoparticles or by adding nanoparticles to a suspension already comprising the antigens. Moreover, in the case where it is desired to have vaccine compositions comprising several types of antigens, it may be preferred to perform in priority the adsorption of certain antigens relative to others. In particular, in the case where the vaccine composition comprises a mixture of antigens, some of which, for reasons of stability or immunogenicity, should not be adsorbed, it may be preferable to proceed in the following manner the aluminum-based particles are first saturated with the antigens requiring adsorption or with ions or excipients present in the buffer substance, before introducing the antigens which should not be adsorbed.

During the preparation of the nanoparticles according to the invention, it is possible for there to be excess polymer. To remove this possible excess of polymer, it is possible to perform an additional step, either directly after the phase of preparing the nanoparticles, or after the phase of mixing with the antigen. This removal phase may be performed by dialysis or diafiltration against demineralized water (Milli Q, Millipore), a saline solution or a biological buffer, through a membrane of adequate porosity (from 30 to 100 kDa according to the size of the nanoparticles).

The examples that follow illustrate embodiments of the invention.

EXAMPLE 1: SYNTHESIS OF A COLLOIDAL SUSPENSION OF PSEUDO-BOEHMITE NANOPARTICLES

Sodium polyacrylate (NaPa) of molecular mass 2100 supplied by Fluka and aluminum chloride hexahydrate ($AlCl_3.6H_2O$) supplied by Avocado were used.

9 g of NaPa were dissolved in 75 ml of aqueous 0.1 M $AlCl_3$ solution. The resulting mixture was stirred vigorously at room temperature for 24 hours. The pH of the mixture was then between 5.5 and 5.9. 5 M sodium hydroxide NaOH was then added dropwise until a pH of 10.5 was obtained, and the mixture was then stirred for a further 10 minutes. When the pH increase reached 9.0-9.5, the solution became slightly turbid, which corresponds to the precipitation of the pseudo-boehmite nanoparticles. To obtain the final nanoparticles, the suspension obtained at pH 10.5 was transferred into an autoclave and heated at 160° C. with gentle stirring (15 rpm) for 3 hours. Next, the colloidal suspension was washed by dialysis against 5 L of distilled water using a Sartorius Slice 200 benchtop machine equipped with a 30 kDa polyether polysulfone membrane. The resulting colloidal suspension was stored in polypropylene bottles. The size measurements performed showed that a single population of nanoparticles was present, the size of which ranged from 15 to 40 nm (numerical distribution), with a polydispersity index of 0.19 (intensity analysis). A sample of solid material was obtained by centrifugation at 25 000 rpm for 1 hour and dried at 80° C. overnight, for physicochemical analytical purposes.

The sample was analyzed by X-ray diffraction by means of a Stoe-Stadi-P diffractometer using the Kα1 line of copper ($\lambda=1.5406$ Å). The radiation is perfectly monochromatic by virtue of the presence of a front monochromator consisting of a germanium crystal. For this analysis, the samples, ground beforehand, are placed in Lindemann tubes (0.3 mm in diameter). The capillary tube, placed on a goniometric head, is rotated and the diffractogram is recorded in Debye-Scherrer mode using a short linear detector of PSD type (position-sensitive detector) able to cover an angular range of 11° (2θ).

The X-ray diffraction analysis of the dried sample gave a result characteristic of pseudo-boehmite.

The nanoparticles obtained were able to be sterile filtered through a 0.2 μm Millipore PVDF membrane, with a minimal loss of material (3.1%) determined by atomic absorption.

EXAMPLE 2: SYNTHESIS OF NANOPARTICLES OF PSEUDO-BOEHMITE AND OF POLYACRYLATE USING A SOLUTION OF SODIUM POLYACRYLATE OF MOLAR MASS 60 000

Sodium polyacrylate (NaPa) of molecular mass 60 000 supplied by Polysciences in the form of an aqueous 35% (w/w) solution and aluminum chloride hexahydrate ($AlCl_3.6H_2O$) supplied by Fluka were used.

In order to obtain 36 g of polymer, 102.86 g of polymer solution which contained 66.86 g of water were taken.

7.2429 g of $AlCl_3$ were placed in a beaker and 225.89 g of water were added thereto. This aluminum solution was added to the polymer solution, so as to obtain 300 ml of a 0.1 M $AlCl_3$ solution.

The mixture obtained was white.

This mixture was stirred vigorously for 24 hours.

After 24 hours, the pH of the mixture was 6.1. 5 M sodium hydroxide NaOH was then added dropwise up to a pH of 10.2.

The mixture was homogenized with stirring for 1 hour and then placed with stirring (1400 rpm) in an autoclave and heated at 160° C. for 3 hours.

The solution obtained was slightly opalescent, and was analyzed to show that it consisted of nanoparticles having by X-ray diffraction peaks characteristic of pseudo-boehmite, and a mean size of about 100 nm, compatible with sterilizing filtration.

The solution was able to be stored for more than 1 year while maintaining the integrity of the nanoparticles, which did not reaggregate.

EXAMPLE 3: PREPARATION OF A VACCINE COMPOSITION COMPRISING NANOPARTICLES OF ALUMINUM HYDROXIDE AND PURIFIED TETANUS PROTEIN, AND FILTRATION TEST

A vaccine composition was prepared by adding 10 μl of a preparation of purified tetanus protein assayed at a concentration of 1200 flocculation units/ml of saline solution to 4.5 ml of a pseudo-boehmite nanoparticle suspension prepared according to example 1.

The mixture was stirred moderately and then passed through a PVDF membrane (supplied by Millipore) mounted on a 5 ml plastic syringe.

Measurement of the size of the nanoparticles was performed both before and after the addition of tetanus protein to the nanoparticles; the same size profile was obtained, whether in the presence or absence of protein, which demonstrates that the tetanus protein does not lead to aggregation of the nanoparticles.

Similarly, it was determined that the filtration led to a 3% loss of aluminum, which is entirely acceptable from an industrial viewpoint.

It may thus be concluded that the vaccine compositions according to the invention may be filtered without excessive loss of material on a 0.22 μm sterilizing filter.

EXAMPLE 4: REACTOGENICITY TEST ON MICE OF A COMPOSITION ACCORDING TO THE INVENTION COMPRISING NANOPARTICLES AND INFLUENZA ANTIGENS, ADMINISTERED INTRADERMALLY

Female BALB/c mice were used as animal model for this test, in order to evaluate the local reactogenicity of compositions according to the invention, compared with standard aluminum suspensions.

In this test, the antigen consisted of a trivalent influenza vaccine known as Flu ID stock comprising the inactivated fragmented strains A/Solomon/3/2006 (H1N1), A/Wisconsin/67/2005 (H3N2) and B/Malaysia/2506/2004 at a rate of 150 μg/ml of HA per strain.

Four groups of 10 mice received at an interval of 3 weeks, intradermally, into the inner face of the ear, a sub-optimal dose of 30 μl (i.e. 0.3 μg of HA/strain) of vaccine in the presence or absence of an adjuvant.

The administered compositions were prepared in the following manner:
  Group A: Flu ID alone; 54 μl of Flu ID stock were diluted in 756 μl of PBS buffer.
  Group B: Flu ID+AlOOH; the following were successively added:
    54 μl of Flu ID stock
    604 μl of PBS buffer
    152 μl of a commercial suspension of AlOOH containing 8.01 mg/ml of aluminum (Alhydrogel®)
    The mixture was stirred moderately for 2 hours.
  Group C: Flu ID+AlPO₄; the following were successively added:
    54 μl of Flu ID stock
    463 μl of PBS buffer
    293 μl of a commercial suspension of AlPO₄ containing 4.15 mg/ml of aluminum (AdjuPhos®)
    The mixture was stirred moderately for 2 hours.
  Group D: Flu ID+nanoAlOOH; the following were successively added:
    54 μl of Flu ID stock
    5 μl of H₂O
    76 μl of 10-fold concentrated PBS buffer
    675 μl of a pseudo-boehmite nanoparticle suspension, prepared in the manner described in example 1 and comprising 1.8 mg of Al/ml.
    The mixture was stirred moderately for 2 hours at room temperature.

The mice were monitored each day, and the edemas, the erythemas and the lesions appearing on the ear were graded on an unofficial scale, for 2 weeks after each injection.

Irrespective of the formulation tested, no significant erythema was observed. Similarly, no edema was reported.

However, white/reddish nodules were noted at the point of injection, appearing in the case of the mice which received the compositions comprising standard aluminum, whether with aluminum hydroxide or with aluminum phosphate. However, surprisingly and very interestingly, no nodules were visible on the mice which received a composition according to the invention.

The results relating to the number of mice presenting nodules after administration of the adjuvants comprising the aluminum of the prior art are illustrated in table 1 below:

TABLE 1

| | After the first injection (D0) | | | | | | | | | |
|---|---|---|---|---|---|---|---|---|---|---|
| Adjuvant | D1 | D2 | D3 | D4 | D7 | D8 | D9 | D10 | D11 | D15 |
| AlOOH | 0/10 | 0/10 | 0/10 | 0/10 | 6/10 | 10/10 | 10/10 | 10/10 | 10/10 | 8/10 |
| AlPO₄ | 0/10 | 1/10 | 2/10 | 3/10 | 6/10 | 9/10 | 9/10 | 9/10 | 10/10 | 9/10 |

| | After the repeat injection (D21) | | | | | | | | | |
|---|---|---|---|---|---|---|---|---|---|---|
| Adjuvant | D22 | D23 | D24 | D25 | D28 | D29 | D30 | D31 | D32 | D35 | D39 |
| AlOOH | 5/10 | 9/10 | 10/10 | 9/10 | 10/10 | 10/10 | 10/10 | 10/10 | 10/10 | 8/10 | 9/10 |
| AlPO₄ | 9/10 | 9/10 | 8/10 | 7/10 | 9/10 | 10/10 | 10/10 | 10/10 | 10/10 | 10/10 | 10/10 |

It is particularly interesting to note that, despite the fact that the amounts of aluminum are the same (45 μg) in all the groups, formulating the aluminum in nanoparticles according to the invention makes it much better tolerated.

EXAMPLE 5: IMMUNOGENICITY TEST ON MICE OF A COMPOSITION ACCORDING TO THE INVENTION COMPRISING NANOPARTICLES AND INFLUENZA ANTIGENS, ADMINISTERED INTRADERMALLY

This test evaluated the immunogenicity of the compositions according to the invention compared with compositions comprising standard aluminum, either AlOOH or AlPO₄, but also with regard to a composition not comprising any aluminum but only polymer. In this test, as in the preceding example, the antigen consisted of a trivalent influenza vaccine known as Flu ID stock comprising the inactivated fragmented strains A/Solomon/3/2006 (H1N1), A/Wisconsin/67/2005 (H3N2) and B/Malaysia/2506/2004 at a rate of 150 μg/ml of HA per strain. The batch of Flu ID stock vaccine used for this test was the same as that used in the preceding example.

The test was performed on female BALB/c mice divided into five groups of 9.

Each mouse received, at an interval of 3 weeks, intradermally, into the inner face of the ear, a sub-optimal dose of 30 μl (i.e. 0.3 μg of HA/strain) of a composition as described below, as a function of the group to which it belonged.

The administered compositions were prepared in the following manner:

Group A: Flu ID alone; 54 μl of Flu ID stock were diluted in 756 μl of PBS buffer.
Group B: Flu ID+AlPO$_4$; the following were successively added:
  54 μl of Flu ID stock
  463 μl of PBS buffer
  293 μl of a commercial suspension of AlPO$_4$ containing 4.15 mg/ml of aluminum (AdjuPhos®)
The mixture was vortexed for 10 seconds.
Group C: Flu ID+AlOOH; the following were successively added:
  54 μl of Flu ID stock
  595 μl of PBS buffer
  161 μl of a commercial suspension of AlOOH containing 7.53 mg/ml of aluminum (Alhydrogel®)
The mixture was vortexed for 10 seconds.
Group D: Flu ID+pseudo-boehmite nanoparticles; the following were successively added:
  54 μl of Flu ID stock
  5 μl of H$_2$O
  76 μl of 10-fold concentrated PBS buffer
  675 μl of a pseudo-boehmite nanoparticle suspension, prepared in the manner described in example 1 and comprising 1.8 mg of Al/ml.
The mixture was vortexed for 10 seconds.
Group E: Flu ID+polymer; the following were successively added:
  54 μl of Flu ID stock
  5 μl of H$_2$O
  76 μl of 10-fold concentrated PBS buffer
  675 μl of a solution containing 17 mg/ml of NaPa (sodium polyacrylate) of molar mass 2100 supplied by Fluka.
The mixture was vortexed for 10 seconds.
The mice were monitored throughout the test.

Blood samples were taken from each mouse at D42, i.e. 3 weeks after the second injection, by sectioning of the carotid vein. The samples were treated in order to isolate the serum to perform the humoral response tests.

The spleens were also taken from six mice per group in order to perform the cell response tests.

The tests that were performed are ELISA assays, hemagglutination inhibition tests, and also ELISPOT assays.

The ELISA assays were performed in a conventional manner, in order to determine the amounts of serum IgG1 and IgG2a specific for the strain A/H1N1. The antibody detection threshold is 20 (1.3 log 10) ELISA units. All the titers are expressed in log 10 of ELISA units. The geometrical mean and the corresponding 95% confidence interval were calculated for each group of animals.

The hemagglutination inhibition test makes it possible to assess the functional antibodies present in the serum of the immunized animals. It measures the capacity of the induced antibodies to inhibit the hemagglutination of hen red blood cells by the influenza virus studied. The hemagglutination inhibition (HI) titer is the inverse of the final dilution for which no hemagglutination is observed. The geometrical mean and the corresponding 95% confidence interval were calculated for each group of animals. This was done with regard to each of the three strains present in the administered composition.

The ELISPOT assays are performed using freshly isolated spleen cells, incubated overnight and restimulated with a mixture of the three strains of the vaccine composition or with a nonamer peptide corresponding to a class I epitope (epitope CD8) of the NP protein. The cell responses are expressed as the number of cells secreting influenza-specific IL-5 or IFN-γ, for $10^6$ splenocytes.

During the restimulation with the influenza-specific peptide, no CD8+ T cells secreting IL-5 or IFN-γ were detected by ELISPOT, irrespective of the group of mice under consideration.

As regards the in vitro restimulation with the influenza antigens, the results obtained are represented in table 2 below, in which the 95% confidence intervals are indicated in parentheses:

TABLE 2

| Group under consideration | Number of cells secreting IL-5/$10^6$ splenocytes | Number of cells secreting IFN-γ/$10^6$ splenocytes |
|---|---|---|
| A: Flu ID alone | 24 [12-48] | 2 [0-17] |
| B: Flu ID + AlPO$_4$ | 17 [6-45] | 2 [0-32] |
| C: Flu ID + AlOOH | 46 [19-115] | 13 [5-38] |
| D: Flu ID + nanoparticles | 197 [79-491] | 79 [30-205] |
| E: Flu ID + polyacrylate | 80 [42-151] | 8 [1-81] |

These results show that, surprisingly, by means of the nanoparticles according to the invention, it is possible to obtain a cell response, especially stimulation of the cells secreting IL-5 and also of the cells secreting IFN-γ.

From a statistical viewpoint, according to a mixed model with Dunnett adjustment, the nanoparticles are considered to have significantly increased the number of cells secreting IL-5 and IFN-γ by 8.2 times (p<0.001) and by 39.5 times (p=0.002), respectively, which is not the case for the aluminum-based adjuvants of the prior art.

It is also noted that polyacrylate alone increased the secretion of IL-5 by only 3.3 times (p=0.027), which is at the significance limit.

The results relating to the humoral response tests are collated in table 3 below, in which, in each case, the 95% confidence intervals are given in parentheses.

TABLE 3

| Group under consideration | HI against H1N1 | HI against H3N2 | HI against B | IgG1 against H1N1 (log10) | IgG2a against H1N1 (log10) |
|---|---|---|---|---|---|
| A: Flu ID alone | 101 [52-194] | 127 [66-244] | 17 [6-46] | 4.8 [4.4-5.2] | 4.3 [3.9-4.6] |
| B: Flu ID + AlPO$_4$ | 1881 [1096-3229] | 1097 [654-1842] | 593 [301-1165] | 6.4 [6.2-6.7] | 4.4 [3.9-4.9] |
| C: Flu ID + AlOOH | 1185 [637-2207] | 1185 [603-2331] | 640 [353-1161] | 6.4 [6.1-6.6] | 4.1 [3.4-4.8] |

TABLE 3-continued

| Group under consideration | HI against H1N1 | HI against H3N2 | HI against B | IgG1 against H1N1 (log10) | IgG2a against H1N1 (log10) |
|---|---|---|---|---|---|
| D: Flu ID + nanoparticles | 1185 [676-2078] | 1613 [1017-2558] | 508 [228-1130] | 6.1 [5.9-6.4] | 5.1 [4.7-5.4] |
| C: Flu ID + polyacrylate | 93 [49-177] | 148 [90-243] | 13 [4-38] | 5.0 [4.8-5.3] | 4.1 [3.7-4.5] |

From a statistical viewpoint, the increase of the HI titers and of the IgG1 titers obtained with the nanoparticles was considered significant with regard to the titers obtained with the vaccine alone according to a mixed model with Dunnett adjustment (11.7 times for the anti-H1N1 HI titer with $p<0.001$; 12.7 times for the anti-H3N2 HI titer with $p<0.001$; 29.9 times for the anti-B titer with $p<0.001$; 20.0 times for the anti-H1N1 IgG1 titer with $p<0.001$ and 6.3 times for the anti-H1N1 IgG2a titer with $p=0.008$).

These results show the capacity of the nanoparticles according to the invention to induce a humoral response after two intradermal immunizations. It may be noted that the polymer alone does not have this adjuvant power.

Moreover, only the nanoparticles according to the invention lead to an increase in the IgG2a response, which means that the immune response profile is more oriented toward a response of TH1 type than for the other aluminum-based adjuvants.

The invention claimed is:

1. A vaccine composition comprising at least one antigen and an adjuvant, wherein the adjuvant comprises nanoparticles comprising pseudo-boehmite and polyacrylate, and wherein the size of the nanoparticles is such that they are able to pass through a sterilizing filter of 220 nm size pore.

2. The vaccine composition as claimed in claim 1, wherein the core of the nanoparticle consists essentially of pseudo-boehmite and the polyacrylate is located essentially at the surface of the nanoparticles.

3. The vaccine composition as claimed in claim 1, wherein the pseudo-boehmite is at least 90% of the mass of the nanoparticles.

4. The vaccine composition as claimed claim 1, wherein the size of the nanoparticles is less than 300 nm.

5. The vaccine composition as claimed in claim 1, wherein the composition comprises at least one influenza antigen.

6. The vaccine composition as claimed in claim 1, wherein the composition comprises at least one tetanus protein.

7. A method of making a vaccine composition comprising combining nanoparticles comprising pseudo-boehmite and polyacrylate with at least one antigen, wherein the size of the nanoparticles is such that they are able to pass through a sterilizing filter of 220 nm size pore.

8. The method of claim 7, wherein the vaccine composition is formulated for intradermal administration.

9. The method of claim 8, wherein the vaccine composition comprises at least one influenza antigen.

10. A process for preparing a vaccine composition as claimed in claim 1, the process comprising,
preparing nanoparticles comprising pseudo-boehmite and polyacrylate, wherein the size of the nanoparticles is such that they are able to pass through a sterilizing filter of 220 nm size pore,
filtering said nanoparticles by means of a sterilizing filter,
adding at least one vaccine antigen to said nanoparticles, and, optionally, performing an additional filtration.

11. The vaccine composition as claimed in claim 2, wherein the size of the nanoparticles is less than 220 nm.

12. The vaccine composition as claimed in claim 11, wherein the pseudo-boehmite is at least 90% of the mass of the nanoparticles.

13. The vaccine composition as claimed in claim 12, wherein the composition comprises at least one influenza antigen.

14. The vaccine composition as claimed in claim 13, wherein the composition comprises at least one tetanus protein.

15. The method of claim 7, wherein the size of the nanoparticles is less than 220 nm.

16. The method as claimed in claim 15, wherein the pseudo-boehmite is at least 90% of the mass of the nanoparticles.

17. The method as claimed in claim 16, wherein the composition comprises at least one influenza antigen.

18. The method as claimed in claim 16, wherein the composition comprises at least one tetanus antigen.

* * * * *